United States Patent [19]

Sarstedt

[11] 4,021,124
[45] May 3, 1977

[54] VESSELS FOR THE OPTICAL OBSERVATION OF LIQUIDS
[75] Inventor: Walter Sarstedt, Numbrecht, Rommelsdorf, Germany
[73] Assignee: Kunststoff-Spritzgusswerk, Germany
[22] Filed: Feb. 25, 1976
[21] Appl. No.: 661,084
[30] Foreign Application Priority Data
Feb. 27, 1975  Germany ................. 2508527
[52] U.S. Cl. .................. 356/246; 250/576
[51] Int. Cl.² ............................ G01N 1/10
[58] Field of Search ........... 356/246; 250/576; 23/292

[56] References Cited
UNITED STATES PATENTS
3,627,432  12/1971  Bergmann ............ 356/246
3,691,017  9/1972   Brown et al. ........ 356/246 UX
3,964,867  6/1976   Berry .............. 356/246 X Primary Examiner—John K. Corbin
Assistant Examiner—Matthew W. Koren
Attorney, Agent, or Firm—Behr & Woodbridge

[57] ABSTRACT

A vessel is provided for receiving a small quantity of a liquid to be observed optically. The vessel has a body provided with four upstanding side walls of which two opposite walls are transparent and optically true and are intended to lie in the optical path. The other two walls are much closer together so as to reduce the interior volume of the vessel and are provided with external vertical ribs so as to impart a generally square external configuration to the vessel. A U-shaped thermally conductive body is disposed with its bridge portion beneath the bottom of the vessel body and with its limbs upstanding between the ribs and in thermal contact with said other side walls. The vessel can be secured in position by means of the bridge piece which may be of dovetail shape or may be magnetic or provided with a permanent magnet.

7 Claims, 10 Drawing Figures

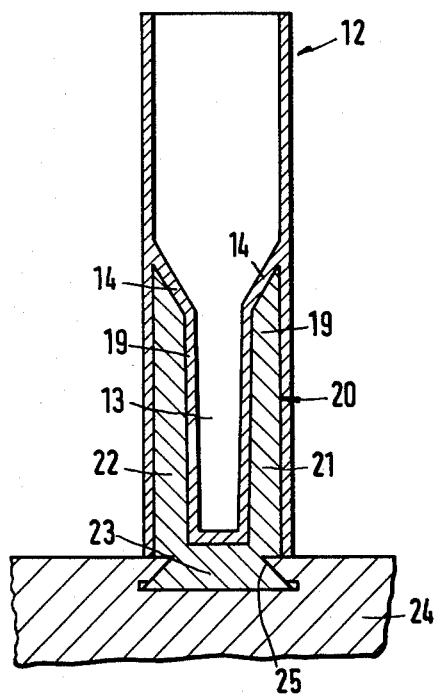
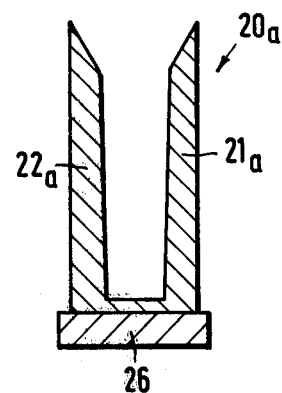
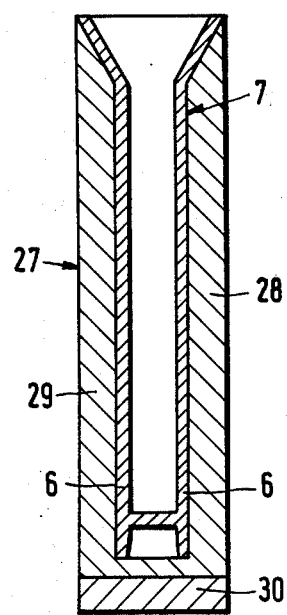
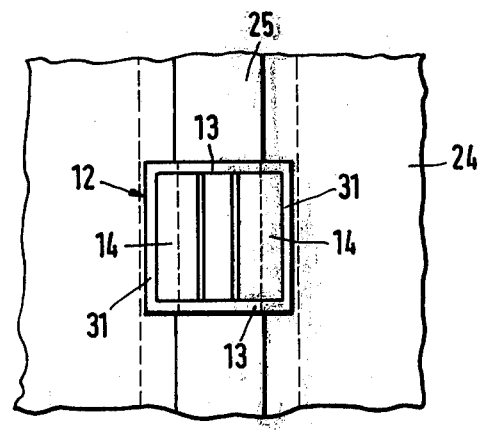

VESSELS FOR THE OPTICAL OBSERVATION OF LIQUIDS

The invention relates to a vessel for the optical observation of small quantites of liquids, having a bottom and four walls which extend therefrom, two of which walls form oppositely located, transparent and planar end walls which extend parallel to one another and which are intended to be disposed in the optical path of observation.

Vessels made from glass or plastics material are known which have a square cross section. The mutually facing walls have a square cross section. The mutually facing walls in the optical path are spaced at a standard distance apart which has been determined in conformity with the measuring method and the following operating device. The other two side walls located at right angles to the optically true walls of these known vessels need not be spaced at the same predetermined distance apart, provided that the vessel is not used such that these other side walls are to be placed in the optical path. However, for the sake of simplicity, a square cross section has been chosen and, consequently, the same spacing has been retained.

The interior space of the vessels should be reduced in the case of certain observations in which only small quantites of the liquid to be observed are available. Since the distance between the side walls in the optical path has been fixed, it was possible to reduce the interior space only by reducing the liquid space in the direction at right angles thereto, i.e. by providing the liquid space with a rectangular cross section. In the case of glass vessels, this was possible in a simple manner by making the side walls not in the optical path considerably thicker than the optically true side walls. The square external cross section of these vessels was then maintained so that even these vessels having a smaller interior space could be inserted into the devices which are provided for this purpose and which has a standard sized reception opening for the vessel.

Whilst glass vessels were usually cemented together from planar plates, the transition from glass to transparent plastics material rendered it desirable to manufacture the vessels in one piece, i.e. by an injection-moulding method. However, adjacently located side walls of greatly differing thicknesses could mot be manufactured by this method. Therefore, a transition was made to the initally mentioned construction in which the optically true side walls are spaced at the predetermined distance apart, while the other two side walls were moved together inwardly and, in order to obtain the square external dimensions of the vessel, their outsides each carried two ribs. These known plastics vessels could then be inserted into the corresponding openings of the measuring devices in the same manner as the glass vessels having a square external cross section. Of course, certain difficulties arose in the case of some devices, since cavities were located between the ribs projecting from each side wall.

A further disadvantage, particularly in the vessels made from plastics material, resides in the fact that, owing to the relatively low thermal conductivity of the plastics material used, preheating to a desired measuring temperature, for example to 25° C or to 37° C, took a longer period of time than in the case of the glass vessels previously used. In particular, the air spaces located between the ribs additionally obstructed satisfactory heat transfer from the outside if these vessels, filled with the liquid to be observed, were placed into a receiving opening of a preheating device.

A feature of the invention is to develop the known vessels with a reduced interior volume for insertion into a reception opening of square cross section, such that satisfactory heat transfer to the side walls surrounding the liquid under observation is rendered possible and thus rapid preheating of the liquid, and at the same time a closed square external cross section is obtained which avoids the difficulties which sometimes occur in the case of the known plastics vessels having ribs upon inserting the vessels into the reception opening of te measuring device.

A vessel according to the present invention for the optical observation of small quantities of liquids comprises a body having a body and four side walls which extend therefrom, two of which side walls form oppositely located, transparent and planar walls which extend parallel to one another and whose outer surfaces are located at a predetermined distance apart, while the other two side walls are spaced a shorter distance apart in order to reduce the quantity of liquid required for examination and each of said other two side walls has on its outside ribs which extend parallel to the transparent and planar walls, the edges of each two mutually aligned ribs being spaced at the said predetermined distance apart, and a substantially U-shaped thermally conductive body, the mutually facing sides of whose limbs abut against said other side walls and each limb fills the space between two adjoining ribs on the respective side wall, while the bridge portion interconnecting the limbs extends below the bottom and serves to releasably secure the vessel to a heating device.

The thermally conductive body is made from a material having satisfactory thermal conductivity, preferably metal, and transfers the heat, received from the outside, to the other side walls not in the optical path but in contact with the thermally conductive body so that the quantity of liquid located between said other side walls is heated more rapidly to the desired temperature.

Since materials of good thermal conductivity, particularly metal, also generally have a relatively high specific heat, the thermally conductive body additionally acts as a heat store and maintains the liquid, which is to be tested, in the range of the desired measuring temperature for a longer period of time. Owing to its satisfactory thermal conductivity and its high specific heat, copper is particularly suitable for manufacturing a thermally conductive body of this type.

In a further development of the vessel in accordance with the invention, it is proposed to interconnect the outer edges of each of two ribs on each of said other side walls by an outer wall to form a receiving pocket for a respective limb on the thermally conductive body. These receiving pockets, open at the bottom, then permit the limbs of the thermally conductive body to be inserted into the plastics body of the vessel from below, while the liquid to be tested is introduced from the top into the space between the side walls.

If connecting walls are not provided, the vessel comprising the plastics vessel body and the thermally conductive body can be heated externally, although, in any event, and in a particularly advantageous manner, it can be heated from the bottom connection bridge of the thermally conductive body. Preferably, the bridge portion of the thermally conductive body is of dovetail configuration at its side romote from the limbs. The dovetail-shaped bridge portion or foot of a vessel of this type can be fitted into a complementary dovetail-shaped groove of a heating device, that is a regulated heating plate, the vessel thus being releasably fixed on the heating plate. After it has been heated to the desired measuring temperature, the vessel is removed from the heating device by pushing the foot laterally out of the dovetail guide, the vessel then being placed into the reception opening or shaft of the measuring device.

Alternatively, for this purpose, the plastics body of the vessel might be removed upwardly from the thermally conductive body, the thermally conductive body being left on the heating device. It is then still possible to take a measurement, although the thermally conductive body then no longer acts as a heat store in order to maintain the liquid, to be tested, for as long as possible in the desired temperature range in the reception opening.

Such removal from the thermally conductive body would, of course, again involve certain disadvantages upon inserting the vessel into certain measuring devices, even in the case of open construction of the plastics body having four laterally projecting ribs which are not interconnected by outer walls since, in this construction, the vessel without a thermally conductive body no longer has a closed square external cross section.

Alternatively, instead of using the aforementioned dovetail fastening, the vessel, that is the bridge portion of the thermally conductive body of the vessel, can be releasably fixed on a heating device by means of a magnetic fastening. For this purpose, it is proposed that the bridge portion of the thermally conductive body should carry a magnet. This magnet then releasably secures the vessel on a heating device having an iron heating plate.

Provided that a heating device having a magnetic mounting plate is available, the bridge portion of the thermally conductive body may alternatively have a plate made from magnetizable material, such as iron. Alternatively, the entire thermally conductive body may be made from a magnetizable material such as iron or nickel.

The invention will be further described hereinafter, by way of example, with reference to the accompanying drawings, in which:-

FIG. 3 is a section, taken on the line III—III of

Figure 4:
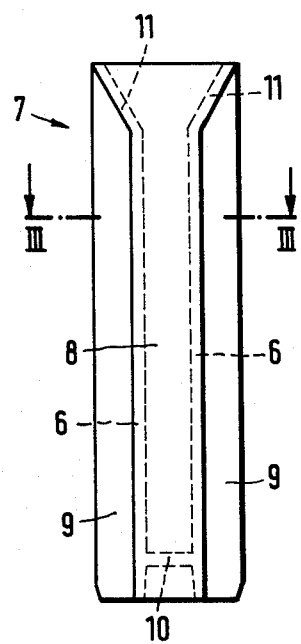
Figure 5:
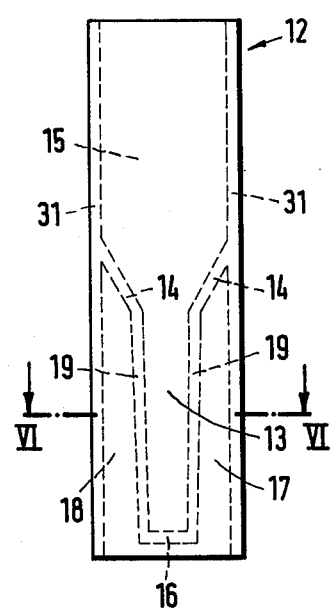
Figure 6:
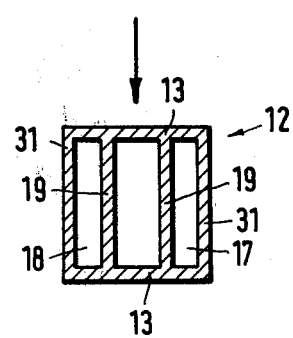

FIG. 4 of a known plastics vessel having a reduced interior space;

FIG. 5 is a front elevation of a vessel in accordance with the invention;

FIG. 6 is a horizontal section taken on the line VI—VI of FIG. 5;

FIG. 7 is a vertical section through a vessel which comprises the plastics body of FIG. 5 and a thermally conductive body of FIG. 9 and which is mounted on a heating plate of a heating device;

FIG. 8 is a plan view of the vessel of FIG. 7 having a heating plate;

FIG. 9 is a vertical section of the thermally conductive body of the vessel shown in FIG. 7, and FIG. 10 is a vertical section of a vessel comprising a plastics body in accordance with FIG. 4 and a thermally conductive body of corresponding configuratin.

Figure 1:
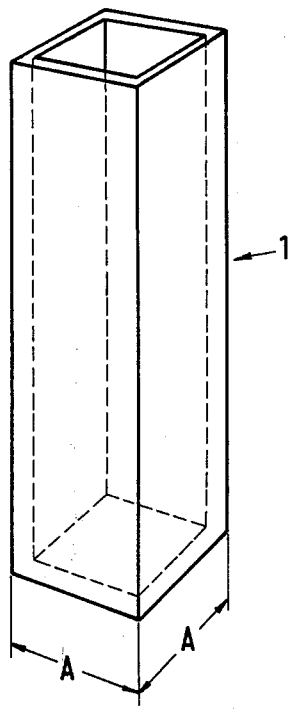
FIG. 1 is a perspective view of a known vessel of square internal and external cross section.

FIG. 1 shows a known vessel 1 for holding fluids to be observed optically. The vessel 1 has square external and internal cross sections and outer edges of a length A and has been cemented together from plane parallel glass plates.

Figure 2:
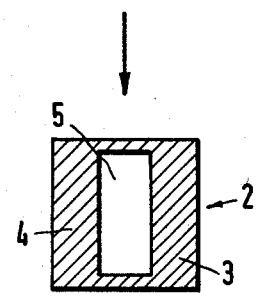
FIG. 2 is a horizontal section through a vessel similar to the vessel shown in FIG. 1, but having an interior space reduced by thickening two of the side walls.

FIG. 2 shows a section through a similar vessel 2 which is to be oriented in an optical observation device (not shown) so that the optical path extends in the direction of the arrow. The interior space 5 has been reduced by making the walls 3 and 4 thicker than the two optically true side walls. Such vessels can be assembled, even if not in one piece, from plates of different thicknesses, although, for the sake of simplicity, this has not been taken into account in FIG. 2.

Figure 3:
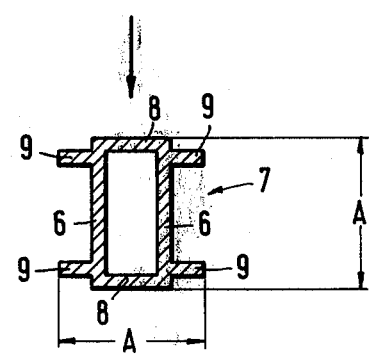

The known plastics vessel 7 illustrated in FIGS. 3 and 4 also has a reduced interior space which is obtained by making the distance between the two side walls 6 not lying in the optical path less than that between the optically true side walls 8 arranged parallel to one another at a standard measured distance apart. Here also, the light is incident in the direction of the arrow. The side walls 6 and 8, together with the bottom 10, form a closed space for receiving the liquid. The top of the receiving space is widened at 11, thus facilitating the introduction of the liquid.

Ribs 9 project outwardly from the side walls 6 and extend parallel to the side walls 8 although they are slightly offset inwardly relative to the side walls 8. The edges of two mutually aligned ribs are spaced apart at a distance A which is equal to the predetermined distance A between the outsides of the optical side walls 8. Consequently, this plactics vessel may be inserted into a corresponding reception opening of a measuring device in the same manner as a vessel having a closed square cross section as shown in FIG. 1 or FIG. 2.

In accordance with one embodiment of the invention, a thermally conductive body 27 is associated with this known plastic body 7 and is assembled with the plastics body in the manner shown in FIG. 10. The thermally conductive body comprises two limbs 28 and 29 which abut snugly against the side walls 6 of the plastics body, and a bridge portion which interconnects the limbs and which, in the embodiment illustrated in FIG. 10, carries a magnetic plate 30 on its underside.

Like the known vessels shown in FIGS. 1 and 2, the vessel illustrated in FIG. 10 has a closed square external cross section. Furthermore, however, this vessel, whose container is made from plastic material, reduces difficulties with respect to heating the liquid from the outside to a predetermined measuring temperature, as well as difficulties when inserting the vessel into a reception opening of a measuring device.

In the vessel illustrated in FIGS. 5 to 9, the plastics body is further developed relatively to the body illustrated in FIGS. 3 and 4 such that the ribs projecting outwardly from the side walls 19 (located nearest to one another) are interconnected by walls 31, so that this plastics body has a closed, square external configuration. As may be seen particularly in FIG. 6, the aforementioned bridge portions, the side walls 19 and the walls 31 form pockets 17 and 18 which, as is shown in FIG. 7, serve to receive the limbs 21 and 22 of the thermally conductive body 20. The pockets 17 and 18 do not extend over the entire height of the vessel, but extend only approximately to the centre thereof where they taper owing to the fact that the side walls 19 of the cavity accommodating the measuring liquid extend outwardly in a funnel-shaped manner at 14 and join the walls 31. The liquid is introduced into the widened upper portion 15 of the plastics body 12 and, during the measuring operation, is located in the lower constricted portion 13 formed by the side walls 19, the optical side walls 13 and the bottom 16.

As is shown in FIG. 7, the thermally conductive body 20 has a dovetail-shaped bridge portion 23 by means of which the thermally conductive body is inserted into a dovetail-shaped groove 25 of a heating plate 24 of a heating device (not shown fully).

This heating device, a portion on which is shown in plan view of FIG. 8, but which is otherwise not the subject of the present invention, can have one or a plurality of such dovetail grooves which can each receive a plurality of vessels located one behind the other in a row.

FIG. 9 shows a different thermally conductive body 20a whose limbs 21a and 22a, are like the limbs of the thermally conductive body 20, made from copper, but which carries an iron plate 26 and is suitable for mounting onto a magnetizable heating plate of a heating device.

I claim:

1. Vessel means for the optical observation of small quantities of liquids, said vessel comprising a vessel body having a bottom and four side walls which extend upwardly therefrom, two opposite ones of said side walls defining transparent and planar end walls which extend parallel to one another and which have outer surfaces located at a predetermined distance apart and the other two of said side walls being spaced apart by a distance less than said predetermined distance in order to reduce the quantity of liquid required for examination, and each having an outer surface on which are defined two ribs which extend parallel to the transparent end walls, each two mutually aligned ones of said ribs having edges which are spaced the said predetermined distance apart, and a generally U-shaped thermally conductive body defining limbs, each limb occupying a space between two respective ribs and having an inwardly facing side which abuts against a respective one of said other side walls, said U-shaped body also defining a bridge portion interconnecting said limbs and extending below said bottom, said bridge portion being adapted to releasably fix the vessel to a heating device.

2. Vessel means according to claim 1, in which said vessel body also has outer walls each interconnecting the outer edges of the two ribs on a respective other side wall to define a receiving pocket to receive a respective limb of the thermally conductive body.

3. Vessel means according to claim 1, in which said bridge portion of the thermally conductive body defines a dovetail configuration at its side remote from said limbs.

4. Vessel means according to claim 1, in which said bridge portion of the thermally conductive body has a magnet thereon.

5. Vessel means according to claim 1, in which said bridge portion of the thermally conductive body has thereon a plate consisting of magnetizable material.

6. Vessel means according to claim 1 in which said thermally conductive body consists of magnetizable material.

7. Vessel means according to claim 1 in which said vessel body consists of an injection moulding.

* * * * *